United States Patent [19]

Szpur

[11] 4,114,263
[45] Sep. 19, 1978

[54] METHOD OF MANUFACTURING MEDICAL ELECTRODES

[76] Inventor: Roman Szpur, 2685 Culver Ave., Dayton, Ohio 45429

[21] Appl. No.: 777,313

[22] Filed: Mar. 14, 1977

[51] Int. Cl.² .......................... A61B 5/04; H01R 9/02
[52] U.S. Cl. ............................... 29/630 R; 29/630 D; 128/2.06 E; 128/417; 128/DIG. 4
[58] Field of Search ............ 29/630 R, 630 D, 630 A, 29/630 C; 128/2.06 E, 2.1 E, 417, 418, DIG. 4

[56] References Cited

U.S. PATENT DOCUMENTS

| | | | |
|---|---|---|---|
| 3,862,633 | 1/1975 | Allison et al. | 128/2.06 E |
| 4,063,352 | 12/1977 | Bevilacqua | 29/630 |

*Primary Examiner*—Carl E. Hall
*Attorney, Agent, or Firm*—Jacox & Meckstroth

[57] ABSTRACT

A sheet of resilient foam material is releasably attached by adhesive to an air impervious carrier sheet and is die cut to form on the carrier sheet an annular pad surrounding a center section. The center section and its corresponding adhesive are removed to define a center opening which receives a molded flexible hub member. The hub member has a top wall which connects with an annular U-shaped channel portion forming an annular hinge and cooperating to define a chamber closed by the carrier sheet. An electrical contact assembly extends from the chamber through the top wall portion of the hub member, and a resilient foam pad or patch containing an electrically conductive gel is confined and sealed within the chamber. The hub member also includes a flexible flange portion which projects outwardly from the U-shaped channel or hinge portion and is permanently bonded or attached to the top surface of the annular pad of resilient foam material.

4 Claims, 3 Drawing Figures

METHOD OF MANUFACTURING MEDICAL ELECTRODES

BACKGROUND OF THE INVENTION

The medical electrode of this invention relates to disposable medical electrodes of the type disclosed in Applicant's U.S. Pat. Nos. 3,696,807, 3,701,346, 3,713,435 and 3,820,531. A plurality of such medical electrodes are normally carried by a sheet or strip of coated paper and are stripped or peeled from the carrier sheet and applied to the skin of an individual or patient. Preferably, the electrode carries an electrically conductive gel which conducts a body generated voltage from the patient's skin to an electrical contact assembly which is connected by a flexible conductor to equipment for monitoring the patient or for producing an electrocardiogram for the patient. Other types of disposable medical electrodes are disclosed in U.S. Pat. Nos. 3,862,633, 3,901,218 and 3,923,042.

In order to minimize the cost of producing such a disposable medical electrode, it has been found highly desirable for the electrode to be constructed in a manner which provides for simplicity and efficiency in manufacturing and which permits a plurality of electrodes to be simultaneously produced in progressive steps with the minimum of labor. In addition, it is important for the electrode to be constructed in a manner which provides for substantial flexing of the electrode so that the electrode will conform to different curvatures or contours of an individual's body and will permit movement and flexing of the skin without the electrode separating from the skin.

Summary of the Invention

The present invention is directed to an improved disposable medical electrode which provides the desirable features mentioned above, and which particularly, is adapted to be economically and efficiently produced in high volume with the minimum of labor in order to minimize the cost of producing the electrode. The electrode of the invention also provides for positively attaching the electrode to practically any contour of the skin surface and for minimizing the resistance to flexing and stretching of the skin.

In accordance with the illustrated embodiment of the invention, the above features and advantages are generally provided by attaching a retaining sheet of resilient porous foam material to a carrier sheet which is coated with an air impervious film of released material. The retaining sheet is die cut down to the carrier sheet to form an annular pad, and the center portion of section of the pad is removed to form a center opening which extends through the pad down to the carrier sheet. A circular hub member is molded from a flexible rubber-like material and includes an annular U-shaped channel portion which forms an integral hinge connection between a center top wall portion of the hub member and an outwardly projecting flange portion.

A snap type electrical contact assembly is clamped to the center of the top wall portion of the hub member and includes a base element which engages a patch of resilient open cell foam material confined within the chamber defined by the annular channel portion of the hub member. The patch carries an electrically conductive gel through which a D.C. current is passed to stabilize the gel with the contact assembly, and the patch engages the coated surface of the carrier sheet. The outer flange portion of the hub member is adhesively bonded or otherwise attached to the upper surface of the annular retaining pad. The hinge effect of the annular channel portion permits the flange portion and the retaining pad to flex substantially in relation to the center top wall portion of the hub member to assure that the electrode conforms easily to the contour of the skin surface and remains attached to the surface for an extended period of time.

Other features and advantages of the invention will be apparent from the following description, the accompanying drawing and the appended claims.

DESCRIPTION OF THE PREFERRED EMBODIMENT

Figure 1:
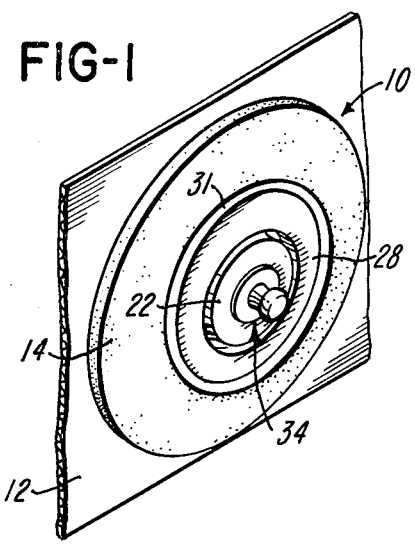
FIG. 1 is a perspective view of a medical electrode constructed in accordance with the invention.

FIG. 1 shows a medical electrode 10 carried by a carrier strip or sheet 12 which may be a plastics impregnated paper sheet having a silicone coating forming an air impervious release surface. Preferably, the coated carrier sheet 12 is cut in the form of a strip having a length sufficient to support three of the electrodes 10.

In accordance with the preferred illustrated embodiment, the medical electrode 10 includes an annular sheet or pad 14 of resilient breathable foam material such as polyvinylchloride foam. However, the pad 14 may also be constructed of other flexible and air permeable material. The pad 14 is releasably attached to the carrier sheet 12 by a layer 16 of pressure sensitive adhesive of the type commonly used on surgical bandages and which does not produce skin irritation. The pad 14 defines a circular center opening 18 which receives a circular hub member 20 molded of a flexible plastics or synthetic rubber material so that the hub member may be easily flexed, twisted or deformed in any direction. The hub member 20 has a durometer within the range of 55 to 65 and preferably on the order of 60.

The hub member 20 includes a circular top wall portion 22 from which depends an annular channel portion 24 having a U-shaped cross sectional configuration. The wall thickness of the channel portion 24 is thinner at the bottom to form an annular integral hinge which permits the parallel side walls of the channel portion to flex with a minimum resistance between a converging relation and a diverging relation. The channel portion 24 cooperates with the top wall portion 22 to define a circular or generally cylindrical chamber 26. The hub member 20 also includes an annular flange portion 28 which projects radially outwardly from the annular channel portion 24 and is positively secured or bonded to the upper surface of the annular pad 14 by an adhesive or by some other means such as heat fusion. The outer edge of the flange portion 28 has an integral peripherally extending rib or rim 31 which helps to assure normal flatness of the flange portion 28.

An electrical snap-type contact assembly 34 is secured to the center of the top wall portion 22 and includes a silver plated brass contact or snap element 36 which may also be made of silver, nickel or aluminum. The contact assembly 34 also includes a conductor element 38 which is preferably molded of a plastics material and is coated with a silver plating. The contact element 38 has a stem portion 39 which projects upwardly through a center hole 41 within the top wall portion 22 of the hub member 20 and is press-fitted into the snap element 36 so that the top wall portion 22 is clamped between the contact elements 36 and 38. The contact element 38 also has a circular base portion 43 which engages a circular pad or patch 45 of open cell resilient foam material such as polyvinylchloride foam. The foam pad or patch 45 is filled with an electrically conductive gel of the type referred to in Applicant's patents mentioned above.

Figure 2:
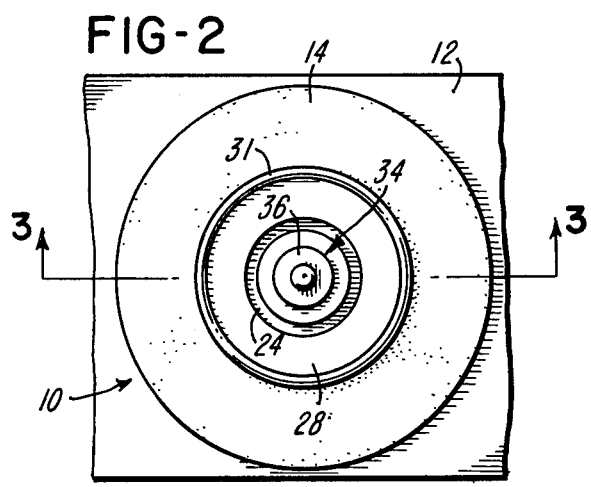
FIG. 2 is a plan view of the electrode shown in FIG. 1.
Figure 3:
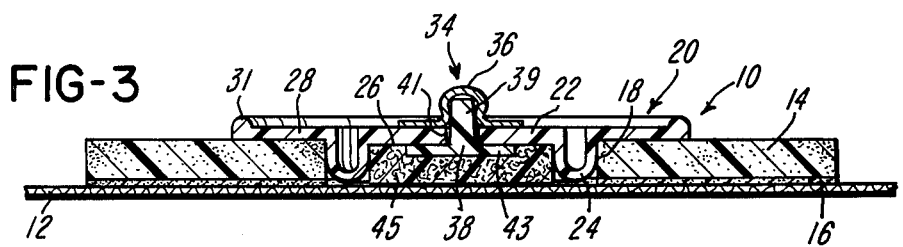
FIG. 3 is an enlarged axial section of the medical electrode, as taken generally on the line 3—3 of FIG. 2.

In the manufacture or production of an electrode as described above and shown in FIGS. 1–3, a sheet or strip of resilient foam material is releasably attached by an adhesive layer 16 to a carrier strip or sheet 12, and the resilient foam sheet is die cut precisely down to the carrier sheet 12 to form the annular pad 14 which may be circular or non-circular. The center circular section of the resilient foam sheet defined within the die cut opening 18 is removed, taking with it the corresponding portion of the adhesive layer 16 attached to the center section of the foam sheet. The contact assembly 34 is clamped to the top wall portion 22 of the molded hub member 20, and the pad or patch 45 of resilient foam material is inserted into the chamber 26 where the patch is secured or retained in contact with the base portion 43 of the contact element 38 by means such as small spots or lines of adhesive (not shown).

The electrically conductive gel is injected into the foam patch 45, and simultaneously regulated DC current is passed through the electrode assembly to chloridize the bottom surface of contact element 38. A coating of adhesive is applied to the bottom surface of the flange portion 28 of the hub member 20 and the assembly of the hub member 20, contact assembly 34 and the filled patch 45 is then inserted into the opening 18 within the center of the foam retaining pad 14. The flange portion 28 of hub member 20 is held in firm contact with the upper surface of the retaining pad 14 until the bonding adhesive sets or the heat fusion is completed.

From the drawing and the above description, it is apparent that a medical electrode constructed in accordance with the present invention, provides desirable features and advantages. For example, the overall simplified construction of the electrode provides for minimizing its production costs and permits a plurality of the electrodes to be efficiently produced simultaneously with automated equipment. As another important feature, the annular hinge formed at the bottom of the U-shaped channel portion 24 of the flexible hub member 20, enables the flange portion 28 to flex easily with the retaining pad 14 so that the retaining pad may conform to any contour of the skin surface and can continue to flex with movement of the skin without becoming detached from the skin.

Thus the flange portion 28 cooperates with the annular retaining pad 14 to assure that the patch 45 and the electrically conducting gel remains in continuous contact with the skin in order to provide a continuous and stable reading to the medical diagnostic equipment connected to the electrode. The passing of a regulated current through the gel and the contact assembly 34 to chlorodize the contact element 38, forms a state of rest between the gel and the contact element so that no electrical charge exists between the gel and the element. It is also apparent that the gel filled patch 45 is confined between the air impervious carrier sheet 12 and the air impervious hub member 20 so that the patch 45 is completely sealed within the airtight chamber 26 until the pad 14 is peeled from the carrier sheet 12 in order to be placed on the skin of an individual or patient.

While the form of medical electrode and its method of production herein described constitutes a preferred embodiment of the invention, it is to be understood that the invention is not limited to this precise form and method, and that changes may be made therein without departing from the scope and spirit of the invention as defined in the appended claims.

The invention having thus been described, the following is claimed:

1. A method of producing a medical electrode adapted to be attached to the skin of an individual, comprising the steps of adhesively attaching a retaining sheet of flexible material to a carrier sheet of adhesive releasing material, cutting through the retaining sheet to only the carrier sheet to form a pad defining an opening confining a separate segment of the retaining sheet, removing the segment of the retaining sheet from the carrier sheet, forming a hub member from a flexible material and with the hub member defining a chamber surrounded by a flange portion, mounting an electrical conductor on the hub member with the conductor extending through to the chamber, locating within the chamber an electrically conductive resilient patch, inserting the hub member and the patch within the opening in the pad, and attaching the flange portion of the hub member to the pad around the opening.

2. A method of producing a medical electrode adapted to be attached to the skin of an individual, comprising the steps of adhesively attaching a retaining sheet of flexible material to a carrier sheet of adhesive releasing material, cutting through the retaining sheet to only the carrier sheet to form an annular pad surrounding a separate segment on the carrier sheet, removing the segment of the retaining sheet and the corresponding adhesive from the carrier sheet to form an opening within the annular pad, molding a hub member from a flexible rubber-like material and with the hub member including a center portion connected to a surrounding flange portion by an annular U-shaped channel portion forming an annular hinge, mounting an electrical conductor on the center portion of the hub member, placing an electrically conductive resilient patch within the channel portion in contact with the conductor, inserting the hub member and the patch within the opening in the pad, and attaching the flange portion of the hub member to the pad around the opening.

3. A method as defined in claim 2 wherein said hub member is molded with the annular U-shaped channel portion having concentric side walls integrally connected by a bottom wall with a relatively thinner wall thickness to form the annular hinge.

4. A method of producing a medical electrode adapted to be attached to the skin of an individual, comprising the steps of adhesively attaching a retaining pad of flexible material to a carrier sheet of adhesive releasing material, attaching to the pad a hub member defining a chamber, mounting an electrical contact element on the hub member with the contact element extending through to the chamber, locating within the chamber an electrically conductive gel, directing an electrical current through the gel and the contact element to form a state of electrical rest between the gel and the contact element, and forming a substantially air tight seal for the gel.

* * * * *